US011210963B2

(12) United States Patent
Baker (10) Patent No.: US 11,210,963 B2
(45) Date of Patent: Dec. 28, 2021

(54) METHOD AND APPARATUS FOR PROVIDING PERSONALISED AUDIO-VISUAL INSTRUCTION

(71) Applicant: Richard John Baker, Queensland (AU)

(72) Inventor: Richard John Baker, Queensland (AU)

( * ) Notice: Subject to any disclaimer, the term of this patent is extended or adjusted under 35 U.S.C. 154(b) by 95 days.

(21) Appl. No.: 15/447,078

(22) Filed: Mar. 1, 2017

(65) Prior Publication Data

US 2017/0206794 A1 Jul. 20, 2017

Related U.S. Application Data

(63) Continuation of application No. 12/311,025, filed as application No. PCT/AU2007/001586 on Oct. 19, 2007, now abandoned.

(30) Foreign Application Priority Data

Oct. 26, 2006 (AU) ................................ 2006905938

(51) Int. Cl.
*G09B 5/06* (2006.01)
*A63B 24/00* (2006.01)
(Continued)

(52) U.S. Cl.
CPC ................ *G09B 5/06* (2013.01); *A61B 5/11* (2013.01); *A61B 5/486* (2013.01);
(Continued)

(58) Field of Classification Search
CPC ..................................................... G09B 5/00
(Continued)

(56) References Cited

U.S. PATENT DOCUMENTS 4,337,049 A 6/1982 Connelly
5,111,410 A 5/1992 Nakayama et al.
(Continued)

FOREIGN PATENT DOCUMENTS

WO WO-0128644 A1 * 4/2001 ............... G09B 5/02
WO WO2002035184 A2 5/2002
(Continued)

OTHER PUBLICATIONS

Office Action dated Nov. 27, 2012, in related Canadian patent application No. 2,700,843.
(Continued)

*Primary Examiner* — William D Ermlick (57) ABSTRACT

A method of and apparatus (10) for providing a personalized audio-visual instructional aid for assisting a person (11) to emulate preferred positions and/or movements in undertaking an activity by capturing position and/or movement data of the person (11) or an object associated with and controlled by the person undertaking the activity using position and/or movement sensing devices such as MEMS sensors (13) on the person (11) or object and using a computer (16) to analyze and compare the captured data with pre-stored data relating to preferred positions and/or movement in undertaking the activity and generating a visual presentation (19) based on the differences between the captured position and/or movement of the person or object and the preferred positions and/or movement and adding to the generated visual presentation, audio instructional comments relating to the differences.

20 Claims, 1 Drawing Sheet

(51) Int. Cl.
    *A63B 71/06*     (2006.01)
    *G09B 19/00*     (2006.01)
    *A61B 5/11*     (2006.01)
    *A61B 5/00*     (2006.01)
    *G06K 9/00*     (2006.01)

(52) U.S. Cl.
    CPC ...... *A63B 24/0003* (2013.01); *A63B 24/0006* (2013.01); *A63B 24/0075* (2013.01); *A63B 71/0622* (2013.01); *G06K 9/00342* (2013.01); *G09B 19/0015* (2013.01); *G09B 19/0038* (2013.01); *A61B 5/1114* (2013.01); *A61B 2503/10* (2013.01); *A63B 2024/0012* (2013.01); *A63B 2220/40* (2013.01); *A63B 2220/51* (2013.01); *A63B 2220/53* (2013.01); *A63B 2220/803* (2013.01); *A63B 2220/836* (2013.01); *A63B 2225/50* (2013.01)

(58) Field of Classification Search
    USPC .................................................. 434/247, 252
    See application file for complete search history.

(56) References Cited

U.S. PATENT DOCUMENTS

| | | | |
|---|---|---|---|
| 5,221,088 A | 6/1993 | McTeigue et al. | |
| 5,300,921 A | 4/1994 | Hoch et al. | |
| 5,486,001 A | 1/1996 | Baker | |
| 5,554,033 A | 9/1996 | Bizzi et al. | |
| 5,694,340 A | 12/1997 | Kim | |
| 5,697,791 A | 12/1997 | Nashner et al. | |
| 5,823,786 A * | 10/1998 | Easterbrook | A63B 24/0003 434/247 |
| 5,836,770 A * | 11/1998 | Powers | A63B 24/0006 434/247 |
| 5,846,086 A * | 12/1998 | Bizzi | A63B 24/0006 434/247 |
| 5,857,855 A | 1/1999 | Midori | |
| 5,907,819 A | 5/1999 | Johnson | |
| 5,984,684 A * | 11/1999 | Brostedt | A63B 24/0003 434/247 |
| 5,984,810 A | 11/1999 | Frye et al. | |
| 6,050,963 A * | 4/2000 | Johnson | A61B 5/1124 600/587 |
| 6,068,559 A | 5/2000 | Lubell et al. | |
| 6,126,449 A | 10/2000 | Burns | |
| 6,159,016 A | 12/2000 | Lubell et al. | |
| 6,416,327 B1 * | 7/2002 | Wittenbecher | A63B 69/3608 434/247 |
| 6,503,086 B1 | 1/2003 | Golubov | |
| 6,514,081 B1 * | 2/2003 | Mengoli | A63B 24/0003 434/252 |
| 6,537,076 B2 | 3/2003 | McNitt et al. | |
| 6,565,448 B2 * | 5/2003 | Cameron | A63B 24/0003 473/131 |
| 6,567,536 B2 | 5/2003 | McNitt et al. | |
| 6,786,730 B2 * | 9/2004 | Bleckley | A63B 24/0003 434/247 |
| 6,905,339 B2 | 6/2005 | DiMare et al. | |
| 7,264,554 B2 * | 9/2007 | Bentley | A61B 5/1122 473/222 |
| 7,404,774 B1 | 7/2008 | Cheng | |
| 7,857,708 B2 * | 12/2010 | Ueda | A63B 24/0003 382/103 |
| 2002/0031753 A1 | 3/2002 | Yanai et al. | |
| 2002/0064764 A1 | 5/2002 | Fishman et al. | |
| 2002/0114493 A1 | 8/2002 | McNitt et al. | |
| 2002/0115047 A1 * | 8/2002 | McNitt | A63B 24/0003 434/252 |
| 2003/0054327 A1 * | 3/2003 | Evensen | A63B 24/0003 434/252 |
| 2003/0109322 A1 * | 6/2003 | Funk | A63B 69/3614 473/222 |
| 2003/0207718 A1 | 11/2003 | Perlmutter | |
| 2004/0152058 A1 | 8/2004 | Browne et al. | |
| 2005/0032582 A1 | 2/2005 | Mahajan et al. | |
| 2006/0057549 A1 | 3/2006 | Prinzel, III et al. | |
| 2007/0190506 A1 * | 8/2007 | Jeng | A63B 24/0087 434/247 |
| 2009/0023122 A1 * | 1/2009 | Lieberman | G16H 20/70 434/258 |

FOREIGN PATENT DOCUMENTS

| | | | |
|---|---|---|---|
| WO | WO2005002436 A1 | 1/2005 | |
| WO | WO-2006135160 A1 * | 12/2006 | ......... A63B 69/3623 |

OTHER PUBLICATIONS

Office Action dated Nov. 14, 2014, in related Canadian patent application No. 2,700,843.

Office Action dated Aug. 31, 2015, in related Canadian patent application No. 2,700,843.

* cited by examiner

METHOD AND APPARATUS FOR PROVIDING PERSONALISED AUDIO-VISUAL INSTRUCTION

The present application is a continuation of patent application Ser. No. 12/311,025 filed Mar. 17, 2009, which is a U.S. national stage application submission under 35 U.S.C. § 371 of International application number PCT/AU2007/001586 filed Oct. 19, 2007, which claims priority to Australian patent application number 2006905938 filed Oct. 26, 2006; all of which are incorporated herein by reference in their entireties.

TECHNICAL FIELD

This invention relates to a method and apparatus for providing personalized audio-visual instruction and in particular to a method and apparatus which uses sensed data coordinates of a human movement or movement of an objoot in order to provide the basis for producing a personalized audio-visual teaching presentation or aid.

BACKGROUND ART

Accurate three-dimensional tracking of human movement has the potential to enable many kinds of human-computer interaction and vision-based methods promise tracking without encumbrance by body-mounted apparatus. The latter form of tracking can be based on the use of optical sensors affixed to a person's body however sensors of this type can become obscured and therefore accurate movement sensing is not always possible. Furthermore, setting up of a movement tracking studio using mocap cameras requires a large area, is very expensive, and for the organizations that do set up these facilities, the data collection procedures are lone and complicated. Each person's test can take up a number of hours and normally requires an engineer (or technician) to be on hand. The data collected can be processed within minutes to yield numerous desired parameters for each application, yet it can take days or weeks for the person being monitored to receive a report on their performance.

The problem with 3D human movement capture is that while it can be very effective for some applications within the confines of a very expensive studio, remote sensing movement systems have not been designed which can be used in general public areas where they are likely to be required such as tennis courts, golf driving ranges, and gyms or in the home environment.

SUMMARY OF THE INVENTION

The present invention aims to provide a method of and apparatus for providing personal audio-visual advice relating to a movement of a person or object. The audio visual advice may be based on prerecorded audio advice or may be personalized and based on input provided by an expert in the field. Other objects and advantages will become apparent from the following description.

The present invention thus provides in one aspect, a method of providing a personalized audio-visual instructional aid for assisting a person to emulate preferred positions and/or movements in undertaking an activity, said method including the steps of capturing position and/or movement data of said person or part of said person or an object associated with and controlled by said person whilst said person undertakes said activity using position and/or movement sensing means attached to or worn by said person or attached to said object, analyzing and comparing said captured t data with pre-stored data of preferred positions and/or movement in undertaking said activity, generating a visual presentation based on the differences between the captured positions and/or movements of said person or object and said preferred positions and/or movements and adding to said generated visual presentation, audio instructional comments relating to said differences to assist a person to emulate said preferred positions and/or movements.

The captured data may comprise coordinate data in at least two axes and preferably three dimensional data that is coordinate data in three axes (x, y and z). The captured data additionally may include orientation data (yaw, pitch and roll).

The method may comprise the step of locally analyzing the data and locally providing the audio-visual instructional aid for viewing by the person. For example the audio-visual aid may be presented on a display screen or screens separate from the person or alternatively incorporated in headwear glasses or goggles worn by the person and the instructional comments provided via headphones or earphones either part of the headwear or separate from the headwear. The data may be analyzed and the audio-visual presentation prepared in apparatus adjacent to or worn by the person.

Alternatively, the method may include the stop of wirelessly transmitting the captured t data to a remote location at which the audio-visual instructional aid based on the pre-stored data is prepared and returned to the person for viewing.

Preferably the captured data is stored in a computer database for comparison with or analysis against the pre-stored data of the preferred positions and/or movements.

Preferably the audio instructional comments are prestored or generated in a database and selected comments from the prestored or generated comments are added to the visual display in accordance with the comparison and analysis between the captured data and prestored data.

The audio instructional comments of the preferred positions and/or movements may be stored in the form of a plurality of comments or phrases relating to the activity being undertaken and to common errors occurring in the activity being undertaken which can be linked automatically to the results of the analysis and comparison between the captured data and prestored data. Thus analysis of the captured data against the prestored data may indicate different positions of the body by the person in undertaking the activity as compared to the prestored preferred position sand an appropriate comment or phrase may be automatically retrieved from the database in accordance with the analysis of the different body positions. The comment or phrase data alternatively may be generated in the database in response to the analysis and comparison of the captured data and prestored data.

The method may further include the step of transmitting the prepared audio visual presentation from the remote location over a communications networks for display on a display screen for direct viewing by the person undergoing instruction. Alternatively the method may include the step of downloading the audio-visual presentation to a storage device such as a memory chip for supply to the person for viewing at a later date.

Preferably the data is captured using sensors which incorporate miniature gyroscopes and/or accelerometers which function by measuring position (x, y, and z coordinates), and orientation (yaw, pitch, and roll) with respect to a reference point or state. Each sensor provides its own global orientation (3 degrees of freedom) and is physically and computationally independent, requiring only external communication. The data however may be captured using other or additions sensors such as magnetometers, OPS sensors or DGPS sensors.

The data from the sensors may be communicated directly or indirectly via wireless via transceiver to a host or server computer for processing which allows a database of the computer which holds the prestored data to receive relatively accurate human or object position or movement data coordinates for processing.

In another aspect, the present invention provides apparatus for providing a personalized audio-visual instructional aid for assisting a person to emulate a preferred movement during an activity, said apparatus including position and/or movement sensing means adapted to be attached to or worn by said person or part of said person or attached to an object associated with and controlled by said person for capturing position and/or movement data of said person or object whilst said person undertakes said activity, means for analyzing and comparing said captured data with pre-stored position and/or movement data relating to preferred positions and/or movements in undertaking said activity, means for generating a visual presentation based on the differences between the captured position and/or movements of said person or object and said preferred positions and/or movements, and means for adding to said generated visual presentation, audio instructional comments relating to said differences to assist a person to emulate said preferred positions and/or movements.

The method and apparatus used for the personalized audio-visual teaching presentation enable a person or pupil to more clearly emulate another movement and receive expert advice to improve their technique without an expert person needing to see the pupil's movement.

As referred to above the sensing means most suitably comprise sensors which incorporate miniature gyroscopes and/or accelerometers. The sensors may comprise one or more of miniature motion sensor such as MEMS (Micro-Electro-Mechanical Systems) sensors, sensors attached to or incorporated in conductive fibres of clothing or-textile fabric which can be worn by a person, magnetometers, GPS and DGPS sensors. Sensors of the above type allow the body movement of a person to be captured and stored for computer analysis.

A common data logging unit may be associated with the sensors to record movement data of the sensors over time. The data logging unit may be a separate unit with which the sensors communicate by hard wiring or wirelessly or the data logging unit may be carried by or worn by the person for example incorporated in a conductive material or fabric which can be embedded or attached to clothing.

Means may be provided for wirelessly transmitting data directly or indirectly from the sensors to a remote location for said analyzing and comparison. Thus wireless transmitters may be associated with each sensor or with the data logging unit for transmission of the data.

The analyzing and comparison means may comprises a computer having a database/s which has/have stored therein pre-stored visual image data representative of the preferred positions and/or movement and wherein the database/s is/are adapted to store the captured data for comparison with the pre-stored data.

The database/s may further include prestored comments or may generate audio instructional comments for addition to the visual presentation.

The computer may include processing means comprising the means for generating the visual presentation based on the analysis and comparison between the stored data of the preferred positions and/or movement and captured data and the processing means is adapted to add to the visual presentation, prestored or generated audio instructional comments based on the analysis and comparison of the data, Means may be provided for transmitting the audio-visual presentation for display on a display screen or downloading to a storage device.

The apparatus may also include means for sensing biomechanical data of the person undertaking the activity and means for incorporating the data in said audio-visual aid.

The apparatus may also include intermediate transceiver means which is adapted to communicate via a communication link with the computer and receive the captured data from the sensing means to convey the data to the computer for analysis and comparison with the prestored data and receive from the computer the audio visual presentation for display to said person.

The transceiver may include a processor and modem or other signal conversion means to permit communication with the computer over the communication link.

The transceiver alternatively may include a database in which the audio-visual aid may be prepared based on information stored in its database and then communicate the prepared aid back to the pupil or person undertaking the activity for display on a screen. The transceiver in this embodiment may be worn or carried by the person undertaking the activity so that immediate instruction may be given.

The present invention has particular applications to teachings in sport, so as to help and assist a person emulate a particular movement or technique. The present invention however may also be applied to many other applications where an emulation or overview of a precise movement is required. Thus, the invention may be applied to various applications in the arts fields, for example the teaching of dance steps or within the medical rehabilitation field where precise movements are required to be performed and expert advice given. Additionally, the present invention may be used in games to detect the movement of a person or their equipment whilst playing a game, analyze that movement against a preferred movement or successful strategies to play the game and show back on screen how they have performed with audio instructional comments to help the player understand where their movement differs from an experts.

The present invention may be further applied to assist drivers to drive a vehicle in a correct and safe manner or to educate persons to follow a correct route. In this latter aspect, sensors may be provided on a vehicle to sense position and movement of the vehicle and the display may be provided in the vehicle and associated with a computer which contains the pro-stored phrases or comments relating to operation of the vehicle. Further sensors such as GPS sensors may be provided on the vehicle to sense position of the vehicle along a road. Alternatively or additionally, sensors on the vehicle may receive data signals from transmitters along the road relating to road restrictions or conditions such as speed limits. That data may be uploaded into the computer for use in providing the presentation. The generated presentation may comprise an audio-visual presentation relating to road conditions or restrictions at that location presented on the screen with instructional comments through any suitable audio output device.

In this latter aspect, the present invention provides a method for providing a personalized audio-visual instructional aid for assisting a person to emulate preferred actions in undertaking an activity in relation to an object controlled by said person, said method including the steps of capturing position and/or movement data of said object whilst said person undertakes said activity using position and/or movement sensing means on said object, analyzing and comparing said captured data with data of preferred positions and/or movements in relation to said activity, generating a visual presentation based on the differences between the captured positions and/or movements of said object and said preferred positions and/or movements and adding to said generated visual presentation, audio instructional comments relating to said differences to assist a person to emulate said preferred actions in said activity.

The aforesaid apparatus may be applied for use in the above method.

BRIEF DESCRIPTION OF THE DRAWING

Reference will now be made to FIG. 1 of the accompanying drawing which illustrate schematically and in block diagram form a preferred embodiment of the invention comprising apparatus for producing audio visual advice to provide an aid to a person undertaking an exercising movement, in this case a simple jumping jack exercise motion It will be appreciated however that whilst the description of the preferred embodiment is made in relation to this specific activity, the present invention may be used in any situation in which coaching for any movement is required.

DETAILED DESCRIPTION OF THE PREFERRED EMBODIMENT

Figure 1:
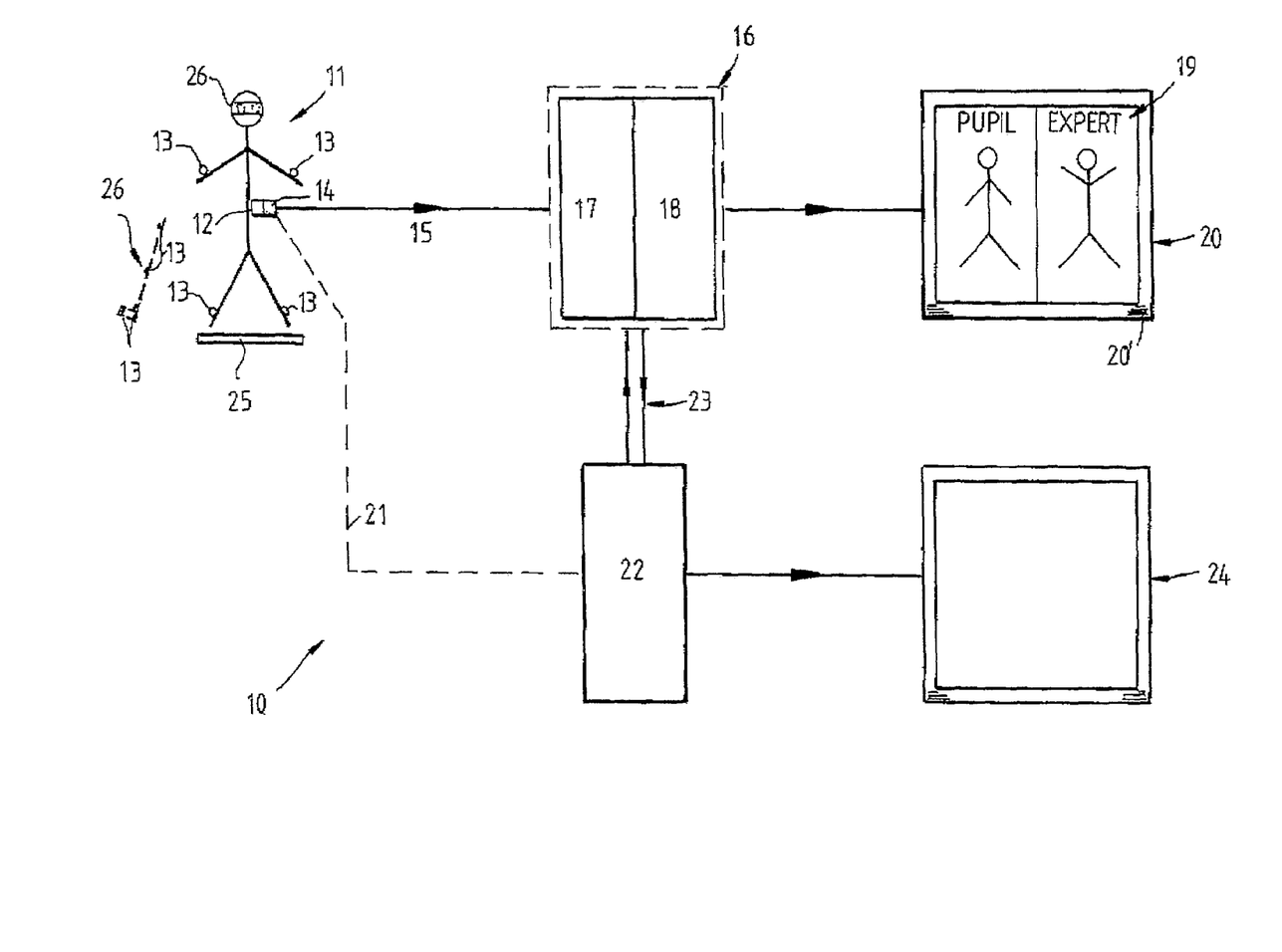

The apparatus 10 as illustrated is described in reference to teaching a pupil 11 an exercise movement in this case a jumping jack, the apparatus 10 includes a data logging unit 12 associated with a plurality of Micro-Electro-Mechanical Systems (MEMS) sensors 13 which can be worn or held by a pupil 11 undertaking an exercise movement in the home or at a sporting facility or the like. The sensors 13 which are affixed to different positions on the pupil's body allow the data coordinates of the pupil's movement and position to be captured. In the embodiment illustrates, sensors 13 are shown on both arms and an both legs however more or less sensors 13 can be used as required depending upon the movement being sensed. Data from sensors 13 as the pupil is undergoing the exercise movement is recorded in the data logging unit 12 and a wireless transmission device 14 is associated with the unit 12 to send the captured data via a communications link or links 15 to a host or server computer 16 having a database 17 in which the transmitted data is stored.

The database 17 additionally has stored therein data relating to an expert's stored movement or a model action or movement. The computer 16 includes a processor 18 which can analyze the data in the database 17 and produce a visual presentation 19 on a display screen or monitor 20 to show the pupil 11 difference in their movement compared with an exports stored movement or model action. The database 17 also stores or can generate a series of prerecorded messages relating to the exercise movement being undertaken. The processor 18 upon analyzing and comparing the recorded data of the pupil 11 relating to their movement with the expert's stored movement can include with the generated visual presentation, audio instructional comments through an audio output device such as a speaker 20' on the monitor or display screen 20 so that the pupil 11 can receive personalized audio-visual coaching or advice as further described below.

To capture the data coordinates of the pupil's exercise, and as referred to above, MEMS sensors 13 with wireless transmission capabilities are used. For this purpose the pupil 11 could wear, hold or have attached to their body or equipment they are using, an array of MEMS sensors 13 which us gyroscopes accelerometers and function by measuring the position (x, y, and z coordinates), and the orientation (yaw, pitch, and roll) with respect to a reference point or state. Each sensor 13 provides its own global orientation (3 degrees of freedom) and is physically and computationally independent, requiring only external communication. More than one MEMs sensor 13 is preferably used attached to different parts of the body to capture the requirement movement and position of the body. Alternatively, the pupil 11 may wear electronic textile clothing that have sensors and interconnections woven into them which can capture a person's movement and position at any point of time. The sensors 13 or clothing however may only be applied to or worn on part of the body (such as to an arm or leg), the movement of which is being analyzed.

The wireless MEMS sensors 13 can directly communicate with the computer 16 or alternatively the information from the sensors 13 can be recorded in the data logging unit 12 which then transmits the data to the computer 16 for storage in the database 17 and subsequent analysis. In the latter case, the data logging unit 12 may be worn on or carried by the person and the MEMS sensors may wirelessly communicate with the data logging unit 12 or be hard wired to the unit 12.

Alternatively, the information from the sensors 13 can as shown in dotted outline be communicated either directly or through the data logging unit 12 wirelessly via wireless link 21 to an intermediate transceiver unit 22 which has its own further two-way communications link 23 with the host computer 16.

The transceiver unit 22 may be an independent unit or take the form of a personal computer, a games box example Playstation, Xbox, Wii, PDA, iPOD, Mobile Phone or the like having its own central processing unit/s and database to which could be added a library of preferred movement images and audio advices so pupil could receive personalized audio-visual instruction directly in a home or training environment without connecting to a chargeable communications network 15 or 23 or to the computer 16. The transceiver unit 22 is preferably of portable construction and may be worn by the pupil 11.

Preferably however the transceiver unit 22 is connectable via modem or other signal conversion device over the communications link 23 to the computer 16 to send information thereto or receive information therefrom to allow the pupil 11 to connect to a much greater library of personalized audio-visual advices which can be stored in the database 17. The computer 16 in this case will analyze the data and prepare the final audio-visual presentation and may be situated anywhere in world whereas in the first instance above the computer 16 maybe in the same room as the pupil or with them as per PDA or iPOD.

The transceiver unit 22 may also include or accept a storage medium such as a memory chip, hard drive or the like for directly making the personalized video or downloading the personalized audio-video instruction made by the remote computer 16 for viewing at a later time. Alternatively, the remote computer 16 may use the transceiver 22 to present the personalized video presentation directly to a display screen 24 connected to the transceiver 22 for viewing by the pupil 11 at the location of the transceiver 22.

The transceiver unit 22 may be software and/or hardware programmed to enable inclusion of one or more of the following features:

1) The sender's details for later personalizing effects to the final video presentation i.e. name and spoken language and means for selecting the person with whom the movement of the person is to be compared.

2) The transmitting parties/agents details for account keeping purposes and security for the system i.e. digitized security code.

3) Circuitry for increased transmission speed.

4) Circuitry and displays for showing details regarding signaling times to reach database and regeneration times once retransmitted back to pupil/agent remote location, for account keeping purposes.

5) Circuitry and displays for showing format of transmitted or requested signals in i.e. PAL, NTSC or SECAM etc.

6) Circuitry for Time, Date, Auto Dial-Redial, Stop, Start, Receive, Send and possibly an Advertising channel etc.

7) Circuitry and displays for showing to whom the regenerated signals belong and to enable the retransmitted regenerated signal to be added to the already prerecorded signal, described below, if desired.

Where recording of movement's takes place, bio-mechanical data such as weight transference, alignment, grip pressure exerted during an exercise movement or the like may also be captured from sensors such as a sensor mat 25 upon which the pupil 11 is exercising, or other load or impact sensor which for example may be incorporated in shoes worn by the person or in the handle of an article being gripped by a person such as in the handle of a golf club. This data may also be transmitted to the transceiver unit 22 or directly to computer 16 for example via the data logging unit 12 so a pupil can then receive with the final audio-visual presentation graphs showing for example, weight transference compared to experts movement.

The communications networks 15 and 21 and 23 may comprise fast spaced cable, wireless, ethernet, general switched telephone network, power line, satellite or the like over which the captured data coordinate signals representative of the pupils movement together with their bio-mechanical data can be transmitted to the computer 16 for storage in the database 17 for later analysis against selected preferred movement signal.

The computer 16 can be in close proximity to the pupil 11 within the same location and be contactable by local wireless or other communications network or be at a remote location which can be contacted by telecommunications means such as via the transceiver 22. In another form, the computer 16 may be portable and worn by the person undertaking the activity. In this form, the computer 16 may include or incorporate the data logging unit 12. In this form, the sensors 13 may wirelessly communicate with the computer 16 or hard wired to the computer 16. The audio-visual aid in this embodiment may be presented for viewing on a monitor or other display adjacent to the pupil or may be presented for viewing on apparatus worn by the pupil such as goggles 26 incorporating a viewable screen The computer database 17 holds the following prerecorded information in digital form, which provides a basis for forming a personalized audio-visual teaching presentation.

1) A digitized audio and visual library of selected coaches, advisers professional or mechanisms movements, techniques, steps or procedures, that have been previously analyzed, recorded and reformed into suitable digitized signals, for later analysis and regeneration in the database against the pupils coordinate signal received.

2) A digitized bio mechanical library of selected coaches or mechanisms movements measured individually or as a group, for later display with the regenerated audio visual signal.

3) A digitized visual library of objects which a comparison can be made against a person's submitted object design sensed via remote sensing means.

The computer 16 is able to receive and edit the transmitted data coordinates or bio-mechanical signals relating to the exercise movement of the pupil 11 and arranges that information in the database 17 in such a way as to be able to match the received data coordinate information with the previously stored and selected database coordinate information of the preferred expert's movement to enable the processor 18 to generate the visual presentation which enables the pupil to see those differences that exist between the two movements, that of the pupil and selected coach.

The computer 16 is software and/or hardware programmed to compare by use of its processor 18 the respective coordinate movement of the person or object being analyzed against the selected preferred movement coordinate with adjustments made such as for size of person, speed and other parameters to allow a correct comparison. The differences between the movement coordinates of the pupil and coach are measured by sampling or other techniques in the database 17 and the processor 18 can then produce automatically a visual representation showing the pupil's movement against the expert's preferred movement.

During the above visual production, the processor 18 can add via software and/or hardware to the visual display previously stored, audio comments from an expert as to how they have performing the movement or how they can improve the movement, so that the pupil can receive in the final audio-visual presentation, personalized audio-visual instruction from an expert, similar to private instruction.

The computer 16 may further include a means for converting received data coordinate signals, if needed, in one broadcasting mode, into those of other countries i.e. PAL-NTSC-SECAM etc. To accomplish this within the computer 16, a Standards Converter or the like may be used, using Optical Scan or Digital Standards features or the like.

The computer 16 may additionally include a means for determining costing on each and every received and regenerated data signal that passes through the system, based upon the following information: —

(a) Signal transmission time to and from the computer database.

(b) The amount of analysis and regeneration time required, for each and every presentation, such as with the showing of audio visual faults, bio-mechanical/characterized data graphs, dialogue and broadcasting changes etc.

The computer 16 is software and/or hardware programmed to accept digitized data signals transmitted to it, associated with the transceiver unit 22, so as to personally relate in the final regeneration and editing phases to the pupil 11, this being performed by, using various digital editing techniques and procedures as described below.

The visual aspect of the audio visual presentation generated by the processor 18 can take the form of split-screening as shown in the drawings generating new visual images of the preferred technique displayed alongside the present technique. Alternatively, the preferred technique can be superimposed over the recorded technique. The visual aspect however may be displayed in any other form. Graphics, charts numbers etc, for bio-mechanical/information displays so that the viewer can clearly see those changes that are required or need to be performed, to develop or pursue the preferred movement, procedure or proposal are also displayed. These superimposing effects or the like, may take the form of a computer generated human body shape appearance, normal human or visual appearance, stick figures etc, so as to show the viewer any variances between their movement and the preferred movement. For case of editing the subject material within the computer database 17, a time code or the like, maybe also burnt into the original recorded signal, so as to make final editing much more efficient within the database 17. This procedure may also be linked with an edit controller or the like, within the computer 16 and processor 18 which locks the two signals electronically together during edits.

To personalize the final presentation, dialogue is also added when required so that the selected instructor or adviser may relate to the viewer/pupil more personally than with other audio-visual presentations. Part of this personalizing effect is initially accomplished in the original transmission phase, by the name, spoken language, broadcasting mode or location statistics etc of the final viewer being captured within this database, to which an addition of dialogue from a selected adviser can also be added by the processor 18 when required in the visual signal generation phase, showing those changes they need to perform or consider, to obtain the preferred movement, thus totally personalizing the return audio-visual signal to the pupil.

The dialogue may take the form of a brief statement, example "keep your arms up like mine when doing this jumping jack" so as to make the viewer fully aware of those changes that are required, or need their consideration, to perfect the movement or procedure. The means for adding such dialogue may take the form of a voice energy monitor, text to speech software or the like contained within the computer database 17 which on analysis can scan a memory bank of stored experts comments or learned words phrases etcetera which maybe in text format within the computer database 17 to find suitable terms to bring attention to these problem areas or matters needing their attention. Dialogue may also be added to the final to audio-visual presentation to suitability of equipment being used to perform the desired movements and techniques.

To increase the systems acceptance as a true teaching aid, scientific data may be presented to a viewer, when needed, in the form of graphs, charts, or the like, set above, below, alongside or within the total regenerated video signal recording. This information is gathered from their received data coordinate signals, being matched to their preferred coaches data coordinate signals contained within the database 17 so that the pupil can clearly see, those bio mechanical differences that exist between, their current procedures techniques and that of their selected coaches professionals procedures techniques.

Once the audio-visual teaching presentation is generated, it is then transmitted back from the computer 16 via communications links 23 to the remote senders or agent's (agent maybe at a training facility providing the service for pupil) transceiver unit 22. This procedure maybe performed, from within the computer 16 itself, using various digital, compression and sampling techniques, or it can be again sent back by a further transceiver associated with the computer 16.

On receipt at the remote pupils/agents receiving location, the audio-visual presentation maybe able to pass through the transceiver unit 22 and be viewed directly an a screen 24 or saved on hard drive, video tape, disk, chip or the like within the transceiver unit 22 or downloaded from the transceiver unit 22 for later viewing or at a web site.

Where the computer 16 is at a remote location and where the transceiver unit 22 is used, the transceiver unit 22 includes the database to store a person or objects movement data coordinates sent to it via wireless means associated with the sensors 13 such as Micro-Electro-Mechanical Systems (MEMS) sensors, other sensors which incorporate gyroscopes and accelerometers which can be attached to or held by the pupil 11 or be part of their equipment. Conductive clothing incorporating similar sensors may also be worn by the pupil 11 to capture the movement data coordinates. The transceiver unit 22 is able to transmit the data coordinates via the communications links 23 to the computer 16, the database 17 of which has previously stored coordinates of a correct movement and audio advice on how to achieve a preferred movement. This advice may also be generated by computer processing facility not needing an expert person to record audio comments. The computer 16 uses various software and hardware techniques to analyses the pupils received motion data coordinates against the preferred stored data motion coordinates of an expert movement and produces within the database 17 a visual presentation showing differences in the pupils movement against the preferred movement. The system whilst making the visual presentation also selects and adds stored audio comments to parts of the visual presentation so a pupil can not only see differences in their movement as opposed to an expert or preferred movement but also can hear an experts audio comment coming via speakers, head phones or other audio output device.

The audio-visual presentation transmitted from computer database 17 back to the pupil via communications link 23 may show the pupil or objects movement in the form of a stick figure or computer generated likeness to normal appearance either superimposed split screened or the like alongside the preferred movement with pointers lines or the like drawn on the visual images to bring attention to areas of fault. To this presentation could also be added graphs or charts to show differences say in weight transference, pressure in grip, equipment being used or the like.

For teaching an exercise movement via the system maybe as follows:

The pupil 11 puts on garment which includes conductive material embedded into it or attaches Micro-Electro-Mechanical Systems (MEMS) sensors 13 to their body or equipment or holds devices which includes these MEMS sensors 13. As the pupil 11 makes an exercise movement these sensors 13 communicate the pupils movement data coordinates wirelessly directly or indirectly via the data logger 12 to the transceiver unit 22 which could also connect to make larger communications network to alert a computer 16 that this pupil 11 would like to receive personalized audio-visual coaching for this particular movement which maybe a jumping jack exercise and the selected coach could be Jane Fonda.

As the pupil 11 is performing the movement their movement data coordinates are captured via the sensors 13 and sent in real time to the computer 16 for storage in the computer database 17 with the processor 18 then analyzing the pupils jumping jack exercise movement against Jane Fonda's preferred way of doing the movement. The computer 16 then produces in near real time using its processor 18, a visual presentation 19 which shows the pupil 11 their movement against the preferred way of doing the movement.

When the computer 16 detects faults, from analyzing the data coordinates of pupil's movement against Jane movement it selects Jane's stored audio comment for this fault from the database 17 and adds it to the new visual presentation so the pupil receives personalized audio-visual instruction from Jane as if she viewed the movement.

For example the audio comments may be "you are not getting your hands over your head! Keep your hands over your head like mine when doing this jumping jack movement, please try again!" The pupil 11 hears this comment whilst watching the video and sees how their movement compares to Jane. Then they would try the movement again.

Bio mechanical data in the form of graphs or charts etc. may also added to the presentation so pupil can clearly see scientific data pertaining to the performed movement. Dialogue may also be added regarding suitability of equipment being used at this stage.

Towards the conclusion of this audio-visual presentation, the expert could conclude by saying: "Thank you for allowing me to help you improve your technique, but please continue to work on these points with the help of your local adviser, who is also there to assist you in overcoming these problems Jane"

The above embodiment has been described with reference to an exercise movement; however, as previously stated the invention may readily applied where other movements are required to be emulated. Such movement may comprise movements of persons or objects, parts or mechanisms. In this embodiment and as before an object may have MEMs motion sensors attached or wear conductive movement sensing material or the like to which gives its position (x, y, and z coordinates), and the orientation (yaw, pitch, and roll) with respect to a reference point or state and as before the data obtained is stored and then transmitted to for storage in a database for analysis in a computer with the corresponding data of a preferred object whose data information is previously stored in the database. A typical object with which the apparatus may be used may comprise a golf club 26 (shown in dotted outline) which carries the sensors 13.

After comparison and adding, where appropriate, suitable dialogue from say an expert in that field, a personalized audio-visual presentation is made and transmitted back to the pupil 11 so that the pupil 11 has an expert assessment of the differences between the respective objects. A particular application in this embodiment could be for advising a cyclist if they are peddling correctly to get maximum power, the system could sense via MEMS sensors or conductive material placed on or inside a shoe the shoe angle during the pedal stroke and compare this to an experts movement and give personalized audio-visual advice in this regards It will be apparent that the latter embodiment may be applied to any suitable objects of which analysis is required. The present invention thus provides a method and means for expertly teaching or instructing procedures, strategies, assessments or perceptions in audio-visual form to enable a viewer to more closely emulate calculate or develop techniques suitable to their various applications.

Whilst the above has been given by way of illustrative embodiment of the invention, all such modifications and variations thereto as would be apparent to persons skilled in the art are deemed to fall within the broad scope and ambit of the invention as herein defined by the appended claims.

The invention claimed is:

1. An automatic audio-visual instructional apparatus for assisting a person to emulate a preferred movement in undertaking an activity, said apparatus comprising:

a plurality of gyroscope accelerometer sensors for affixing to said person and/or an object associated with and controlled by said person, each gyroscope accelerometer sensor being physically and computationally independent, and being adapted to capture and process two-dimensional or three-dimensional coordinates, orientation and movement data of said person or the object associated with and controlled by said person whilst said person undertakes said activity;

bio-mechanical sensors for sensing bio-mechanical data relating to at least weight-transference, alignment and grip pressure of the person undertaking said activity;

a data logging unit associated with the gyroscope accelerometer sensors and the bio-mechanical sensors for receiving captured data, comprising processed two-dimensional or three-dimensional coordinates, orientation, movement and the bio-mechanical data from the plurality of gyroscope accelerometer sensors, and the bio-mechanical sensors;

a computer device in communication with the data logging unit, the computer device comprising a database and a processor, the database being adapted to receive and to store the captured-data from the data logging unit, and to store pre-stored data relating to preferred positions, movement and bio-mechanics in undertaking said activity, the processor being adapted to automatically provide an analysis and a comparison of said captured data with the pre-stored data including a digitized audio instructional and visual library of a plurality of coaches or professionals, a digitized bio-mechanical library of the plurality of coaches or professionals, and a digitized visual library of objects, the processor automatically generating a visual presentation based on differences between the captured data and said pre-stored data and automatically adding to said visual presentation, pre-stored or generated audio instructional comments dialogue, the pre-stored or generated audio instructional comments selected or generated automatically in accordance with said analysis and said comparison of said captured data with said pre-stored data, thereby generating an audio-visual teaching presentation with separate visual bio-mechanical data, said visual presentation including one or more images representing an entire body of a human emulating the preferred movement; and a transceiver unit in communication with the computer device for receiving the audio-visual teaching presentation with visual bio-mechanical data.

2. Apparatus as claimed in claim 1 wherein said gyroscopic accelerometer sensors comprise one or more Micro-Electro-Mechanical Systems (MEMS) sensors, which are connected to or incorporated in clothing to be worn by said person, and which comprise one or more of magnetometers, GPS and DGPS (Differential GPS) sensors.

3. Apparatus as claimed in claim 1, wherein the transceiver is adapted to communicate via a communication link with said computer and receive said captured data and convey said captured data to said computer device for said analysis and said comparison with said pre-stored data and receive from said computer device said audio-visual teaching presentation in a format suitable for display to said person.

4. Apparatus as claimed in claim 3, wherein said transceiver includes a transceiver processor and a modem or other signal converter for sending the captured data to the computer device and for receiving the audio-visual instructional presentation from said computer device over said communication link.

5. The apparatus as claimed in claim 1 further comprising a display screen, wherein the transceiver unit is configured to transmit the audio-visual teaching presentation to the display screen for direct viewing by the person.

6. The apparatus according to claim 1, wherein the bio-mechanical sensors comprise bio-mechanical movement sensors for generating bio-mechanical movement data; and wherein the pre-stored data comprises pre-stored movement data.

7. The apparatus according to claim 1, wherein the pre-stored or generated audio instructional comments comprise spoken words or phrases which informs the person.

8. A method of providing a personalized audio-visual instructional aid for assisting a person to emulate preferred positions and/or movements in undertaking an activity, using an automatic audio-visual instructional apparatus as claimed in claim 1, said method including the steps of:
    a) capturing position and movement data of said person or part of said person or an object associated with and controlled by said person whilst said person undertakes said activity, using a plurality of gyroscope accelerometer sensors, and a plurality of bio-mechanical sensors attached to or worn by said person or attached to said object,
    b) automatically analyzing and comparing said captured-data with pre-stored data relating to the preferred positions and movements in undertaking said activity,
    c) automatically generating a visual presentation based on the differences between the captured data and said pre-stored data and automatically adding to said visual presentation, pre-stored or generated audio instructional comments selected or generated automatically in accordance with said analysis and said comparison of said captured data with said pre-stored data for presentation to said person to assist said person to emulate said preferred positions and movements, said visual presentation including one or more images representing an entire body of a human emulating the preferred positions and/or movements.

9. The method according to claim 8, wherein the bio-mechanical sensors comprise bio-mechanical movement sensors for generating bio-mechanical movement data; and wherein the pre-stored data comprises pre-stored movement data.

10. The method according to claim 8, wherein the pre-stored or generated audio instructional comments comprise spoken words or phrases which informs the person.

11. An automatic audio-visual instructional apparatus for assisting a person with a personalized audio-visual instructional presentation to emulate a preferred movement in undertaking an activity, said apparatus comprising:
    a plurality of gyroscope accelerometer sensors for affixing to said person and/or an object associated with and controlled by said person,
    each gyroscope accelerometer sensor being physically and computationally independent, and being adapted to capture and process two-dimensional or three-dimensional coordinates, orientation and movement data of said person or the object associated with and controlled by said person whilst said person undertakes said activity;
    a data logging unit associated with the gyroscope accelerometer sensors for receiving captured data comprising the processed two-dimensional or three-dimensional coordinates, orientation, movement and data from the plurality of gyroscope accelerometer sensors;
    a computer device in communication with the data logging unit, the computer device comprising a database and a processor,
    the database being adapted to receive and store the captured data from the data logging unit, and adapted to store pre-stored data relating to preferred positions and movement in undertaking said activity,
    the processor being adapted to automatically provide an analysis and a comparison of said captured data with the pre-stored data including a digitized audio instructional and visual library of a plurality of coaches or professionals, and a digitized visual library of objects, the processor automatically generating a visual presentation based on differences between the captured data and said pre-stored data and automatically adding to said visual presentation, pre-stored or generated audio instructional comments selected or generated automatically in accordance with said analysis and comparison of said captured data with said pre-stored data, thereby forming an audio-visual teaching presentation, said visual presentation including one or more images representing an entire body of a human emulating the preferred movement; and
    a transceiver unit in communication with the computer device for receiving the audio-visual teaching presentation.

12. The apparatus of claim 11 further comprising bio-mechanical sensors that senses physical, mechanical or object movement.

13. The apparatus according to claim 11, wherein the bio-mechanical sensors comprise bio-mechanical movement sensors for generating bio-mechanical movement data; wherein the pre-stored data comprises pre-stored movement data; and wherein the pre-stored or generated audio instructional comments comprise spoken words or phrases which informs the person.

14. An automatic audio-visual instructional apparatus for assisting a person to emulate a preferred movement in undertaking an activity, said apparatus comprising:
    a plurality of gyroscope accelerometer sensors for affixing to said person and/or an object associated with and controlled by said person,
    each gyroscope accelerometer sensor being physically and computationally independent, and being adapted to capture and process two-dimensional or three-dimensional coordinates, orientation and movement data of said person or the object associated with and controlled by said person whilst said person undertakes said activity;
    bio-mechanical sensors for sensing bio-mechanical data of undertaking said activity;
    a data logging unit associated with the plurality of gyroscope accelerometer sensors and the bio-mechanical sensors for receiving captured data comprising the processed two-dimensional or three-dimensional coordinates, orientation, movement and bio-mechanical data from the plurality of gyroscope accelerometer sensors, and the bio-mechanical sensors;
    a computer device in communication with the data logging unit, the computer device comprising a database and a processor,
    the database being adapted to receive and store the captured data from the data logging unit, and adapted to store pre-stored data relating to preferred positions, movement and bio-mechanics in undertaking said activity, the processor being adapted to automatically provide an analysis and a comparison of said captured data with the pre-stored including a digitized audio and visual library of a plurality of coaches or professionals, a digitized bio-mechanical library of the plurality of coaches or professionals, and a digitized visual library of objects for comparison with the object, the processor automatically generating a visual presentation based on differences between the captured data-and said pre-stored data and automatically adding to said visual presentation, pre-stored or generated audio instructional comments, the pre-stored or generated audio instructional comments automatically generated in accordance with said analysis and said comparison of said captured data with the pre-stored, thereby generating an audio-visual teaching presentation with separate visual bio-mechanical data, said visual presentation including one or more images representing an entire body of a human emulating the preferred movement; and a transceiver unit in communication with the computer device for receiving the audio-visual teaching presentation with visual bio-mechanical data.

15. The apparatus of claim 14 wherein the bio-mechanical data is selected from the group consisting of: weight transference, alignment, grip pressure, load, impact and physical movement.

16. The apparatus as claimed in claim 14, wherein said plurality of gyroscopic accelerometer sensors comprise one or more Micro-Electro-Mechanical Systems (MEMS) movement sensors, configured to be attached to or incorporated in clothing to be worn by the person.

17. The apparatus as claimed in claim 14, wherein the transceiver is adapted to communicate via a communication link with said computer device, configured to receive said captured data from said plurality of gyroscope accelerometer sensors to convey said captured data to said computer device for said analysis and said comparison with said pre-stored data and receive from said computer device said audio-visual teaching presentation for display to the said person.

18. The apparatus as claimed in claim 17 wherein said transceiver includes an intermediate processor and a modem or other signal converter for sending the captured data to said computer device over said communication link.

19. The apparatus as claimed in claim 14, further comprising a display configured to receive the audio-visual teaching presentation from the transceiver unit.

20. The apparatus according to claim 14, wherein the bio-mechanical sensors comprise bio-mechanical movement sensors for generating bio-mechanical movement data; wherein the pre-stored data comprises pre-stored movement data; and wherein the pre-stored or generated audio instructional comments comprise spoken words or phrases which informs the person.

* * * * *